United States Patent
Hesselballe Hansen et al.

(10) Patent No.: US 8,895,085 B2
(45) Date of Patent: Nov. 25, 2014

(54) AGGLOMERATED OIL IMPREGNATED PSYLLIUM HUSK

(75) Inventors: Tim Hesselballe Hansen, Fredericia (DK); Gunner Jacobsen, Blommenslyst (DK)

(73) Assignee: Biofiber-Damino A/S, Gesten (DK)

( * ) Notice: Subject to any disclaimer, the term of this patent is extended or adjusted under 35 U.S.C. 154(b) by 105 days.

(21) Appl. No.: 13/696,297

(22) PCT Filed: May 5, 2011

(86) PCT No.: PCT/DK2011/050154
§ 371 (c)(1), (2), (4) Date: Nov. 5, 2012

(87) PCT Pub. No.: WO2011/141028
PCT Pub. Date: Nov. 17, 2011

(65) Prior Publication Data
US 2013/0064909 A1   Mar. 14, 2013

(30) Foreign Application Priority Data

May 8, 2010 (DK) ................................. 2010 70195
Feb. 19, 2011 (DK) ................................. 2011 00115

(51) Int. Cl.
*A61K 36/68* (2006.01)
*A61K 36/00* (2006.01)
*A61K 9/14* (2006.01)
*A61K 31/715* (2006.01)
*A23L 1/308* (2006.01)
*A23L 1/00* (2006.01)
*A23L 1/0526* (2006.01)

(52) U.S. Cl.
CPC ............... *A23L 1/308* (2013.01); *A23L 1/0017* (2013.01); *A23L 1/0526* (2013.01); *A61K 36/68* (2013.01)
USPC .............. 424/738; 424/776; 424/489; 514/54

(58) Field of Classification Search
None
See application file for complete search history.

(56) References Cited

U.S. PATENT DOCUMENTS

| | | |
|---|---|---|
| 3,766,165 A | 10/1973 | Rennhard et al. |
| 3,876,794 A | 4/1975 | Rennhard |
| 4,459,280 A | 7/1984 | Colliopoulos et al. |
| 4,548,806 A | 10/1985 | Colliopoulos et al. |
| 4,551,331 A | 11/1985 | Rudin |
| RE32,811 E | 12/1988 | Rudin |
| 5,340,580 A | 8/1994 | Barbera |
| 5,445,831 A | 8/1995 | Leis, Jr et al. |
| 6,312,730 B1 | 11/2001 | Sander |
| 6,500,480 B1 | 12/2002 | Burri et al. |
| 7,026,303 B2 | 4/2006 | Cimiluca et al. |

FOREIGN PATENT DOCUMENTS

| | | |
|---|---|---|
| EP | 1090558 | 4/2001 |
| EP | 1090558 A1 * | 4/2001 |
| JP | 2001086956 | 4/2001 |

OTHER PUBLICATIONS

International Search Report for PCT/DK2011/050154 mailed Jul. 19, 2011 (4 pgs.).

* cited by examiner

*Primary Examiner* — Chris R Tate
*Assistant Examiner* — Russell Fiebig
(74) *Attorney, Agent, or Firm* — Merchant & Gould P.C.

(57) ABSTRACT

There is provided agglomerated oil impregnated psyllium husk and to a method for manufacturing the agglomerated oil impregnated psyllium husk. Specifically the present invention provides compositions comprising agglomerates of psyllium husks, wherein the husks have been subjected to treatment with an oily component (e.g. vegetable oil, such as rapeseed oil) prior to a drying process, such as a fluidized bed process, wherein the husks are agglomerated with a saccharide containing aqueous suspension/solution sprayed onto the husks.

8 Claims, No Drawings

AGGLOMERATED OIL IMPREGNATED PSYLLIUM HUSK

This application is a National Stage Application of PCT/DK2011/050154, filed 5 May 2011, which claims benefit of Serial No. PA 2010 70195, filed 8 May 2010 in Denmark and Ser. No. PA 2011 00115, filed 19 Feb. 2011 in Denmark and which application(s) are incorporated herein by reference. To the extent appropriate, a claim of priority is made to each of the above disclosed applications.

FIELD OF THE INVENTION

The present invention relates to agglomerated oil impregnated psyllium husk and to a method for manufacturing the agglomerated oil impregnated psyllium husk of the present invention.

BACKGROUND OF THE INVENTION

Products containing psyllium husk are known. Such products are useful for the benefit of normalizing bowel function and laxation. In addition, recent research has demonstrated the effectiveness of psyllium seed husk fiber in reducing human serum cholesterol levels and in controlling blood glucose levels in diabetics.

Psyllium seed husk forms a gelatinous mass on contact with water, and it exhibits poor dispersibility and mixability in water. The psyllium husk particles tend to agglomerate when mixed with water or saliva. Hydration takes place over the surface of such agglomerated aggregates to form gel-coated lumps, the interiors of which are still substantially dry. These lumps cause an uncomfortable mouth feel and may be difficult to swallow.

U.S. Pat. No. 5,340,580 discloses agglomerated psyllium husk comprising edible acid uniformly dispersed throughout the agglomerating coating. In a preferred embodiment the patent discloses maltodextrin-containing agglomerates of psyllium husk comprising citric acid uniformly dispersed throughout the maltodextrin coating. This agglomerated psyllium husk has improved mixability and dispersibility in liquids.

U.S. Pat. No. 6,312,730 discloses a rapidly dispersible powder having use as a laxative and fiber supplement, comprising psyllium particles coated with gum arabic. The present invention also includes a method for making the powder that includes providing an effective quantity of gum arabic to a fluidized bed having the psyllium particles to make the rapidly dispersible powder. The present invention further includes a method for making a constipation treatment and a treatment for fiber supplementation.

U.S. Pat. No. 4,548,806 is directed to coating of psyllium husks with a water soluble hydrolyzed starch oligosaccharide, a mono- or di-saccharide, a polyglucose, or a polymaltose to form an agglomerate. The coating or film may be applied by any convenient technology. A preferred method of agglomerating the psyllium husks is by fluid bed agglomeration. Finally, the material may be dried by conventional hot air means; such as fluid bed drying or tray drying. A preferred method of drying is fluid bed drying. Moreover, this prior art document mentions that flavoring agents such as certain volatile oils or other liquid or dry agents which are pharmacologically acceptable may also be incorporated in the composition. Examples of flavoring agents are orange, strawberry and cherry.

U.S. Pat. No. 7,026,303 discloses compositions comprising a plurality of agglomerates comprising a polysaccharide component comprising xylose and arabinose, wherein the ratio of xylose to arabinose is at least about 3:1, by weight; wherein the compositions further comprise: (i) optionally, a first surrounding layer which surrounds the agglomerate, wherein the first surrounding layer is a hydrophobic layer; and (ii) optionally, a second surrounding layer which surrounds the agglomerate, wherein the second surrounding layer is a hydrophilic layer; wherein the compositions comprise at least one of the first surrounding layer and the second surrounding layer, and wherein when the agglomerate comprises the first surrounding layer and the second surrounding layer then the first surrounding layer is a preceding layer relative to the second surrounding layer.

EP 1090558 A1 discloses a psyllium husk product where an intermediate product comprising 84-96% of psyllium husk and up to 8% of oil or fat. The intermediate product is extruded and dried, and following used in a ready-to-eat cereal product together with further cereal products and milk solids. The ingredients are agglomerated with a syrup comprising sugar. The ready-to-eat cereal product comprises 20-50 parts of the psyllium husk intermediate product and 15-40 parts of sugar coating. In an example sunflower oil is used as oil and sucrose as sugar coating.

JP 2001086956 A describes a composition comprising 70-90% of powder of psyllium of *Plantago ovata* Forskal and 2-10% of an oily binder mainly containing glycerine fatty acid esters. The mixture is kneaded, extruded and dried to give fiber-containing granules that do not cause an unpleasant texture when orally administered. In an example, a composition comprising 80.0% of psyllium of *Plantago ovata* Forskal and 4.5% palm oil is prepared.

U.S. Pat. No. 4,551,331 describes a modified dry dietary fiber product having improved dispersibility in liquids. The product comprises 80-99.95% of at least one dietary fiber e.g. psyllium and 0.05-20% of a food grade emulsifier. The product is prepared by mixing the fibrous material with a mixture of emulsifier and a non toxic solvent by various known processes. The solvent is then flashed off. In a further process, the emulsifier and the fiber material is blended without using any solvent.

The above cited prior art documents relate to milled psyllium husk (powder), which inevitably results in a dough (or thermoplastic mass) when mixed with an oil. Such a dough needs to be extruded or cut in some way before agglomeration can take place.

Hence, the prior art does not focus on compositions comprising agglomerates of psyllium husks, wherein unmilled husks have been subjected to treatment with an oily component (e.g. vegetable oil, such as rapeseed oil) prior to a drying process, such as a fluidized bed process, wherein the husks are agglomerated with an saccharide containing aqueous suspension/solution sprayed onto the husks.

It is an object of the present invention to provide oil impregnated psyllium that can immediately (i.e. without the need of extrusion or similar treatment) be agglomerated to obtain free flowing particles.

SUMMARY OF THE INVENTION

The inventors have surprisingly found that when the below recited combination of oil and unmilled psyllium husk is used then a free flowing mass is obtained which upon agglomeration becomes light (low density) and easily ingestible. It is highly surprising that no extrusion is needed before the agglomeration is performed.

The present invention relates to agglomerated oil impregnated psyllium husk comprising:

(a) from 50 w/w % to 90 w/w % unmilled psyllium husk;
(b) from 3 w/w % to 15 w/w % of an oily component impregnating the psyllium husk; and
(c) from 4 w/w % to 40 w/w %, preferably from 10 w/w % to 30 w/w %, of agglomerating material coating on the impregnated psyllium husk.

Preferably the agglomerated oil impregnated psyllium husk comprises or consists of:
(a) from 60 w/w % to 85 w/w % unmilled psyllium husk;
(b) from 4 w/w % to 10 w/w % of an oily component impregnating the psyllium husk; and
(c) from 12 w/w % to 25 w/w % of agglomerating material coating on the impregnated psyllium husk.

More preferably the agglomerated oil impregnated psyllium husk comprises or consists of:
(a) from 65 w/w % to 80 w/w % unmilled psyllium husk;
(b) from 5 w/w % to 8 w/w % of an oily component impregnating the psyllium husk; and
(c) from 15 w/w % to 23 w/w % of agglomerating material coating on the impregnated psyllium husk.

Most preferably the agglomerated oil impregnated psyllium husk comprises or consists of:
(a) from 67 w/w % to 77 w/w % unmilled psyllium husk;
(b) from 5 w/w % to 8 w/w % of an oily component impregnating the psyllium husk; and
(c) from 15 w/w % to 23 w/w % of agglomerating material coating on the impregnated psyllium husk.

In a preferred embodiment of the present invention the oily component is a vegetable oil.

Concerning the agglomerating material this is preferably selected from the group consisting of water dispersible hydrolyzed starch oligosaccharide, monosaccharide, di-saccharide, polyglucose, polymaltose, maltodextrin and mixtures thereof.

The present invention is also directed to a method for producing the agglomerated oil impregnated psyllium husk. In this method the following steps are performed:
(a) impregnating or coating psyllium husk with a thin layer of an oily component;
(b) coating to agglomerate the impregnated psyllium husk with a solution comprising an agglomerating material; and
(c) drying the agglomerated impregnated psyllium husk,
wherein the agglomerated oil impregnated psyllium husk comprise from about 50 w/w % to about 90 w/w % unmilled psyllium husk, from about 3 w/w% to about 15 w/w %, preferably from about 4 w/w % to 10 w/w %, of the oily component and from about 4 w/w % to about 40 w/w %, preferably from about 10 w/w % to about 30 w/w %, of the agglomerating material.

The preferred above recited ranges of constituents in the agglomerated oil impregnated psyllium husk also apply to the method of the present invention.

The present inventors have surprisingly found that the agglomerated oil impregnated psyllium husk of the present invention does not form gel-lumps when in contact with saliva and is easy to swallow. Moreover, the palatability of the agglomerated oil impregnated psyllium husk of the present invention is superior over neat psyllium husk, without compromising storage stability.

DETAILED DESCRIPTION OF THE INVENTION

The psyllium husk used in the present invention is from psyllium seeds, from plants of the *Plantago* genus. Commercial psyllium husk include the French (black; *Plantago indica*), Spanish (*P. psyllium*) and Indian (blonde; *P. ovata*). Indian (blonde) psyllium husk is preferred for use herein.

Also preferred is psyllium husk which is at least about 85% pure, more preferably at least about 90% pure, and most preferably at least about 95% pure. Compositions of the present invention comprise from about 40% to about 95% psyllium husk, preferably from about 50% to about 90%, and more preferably from about 60% to about 80%.

The psyllium husk is obtained from the seed coat of the psyllium seeds. It is typical to remove the seed coat from the rest of the seed by, for example, slight mechanical pressure, and then to use only the seed coat. The seed coat is preferably removed and sanitized by methods known in the art. Preferred is sanitized psyllium seed husk having substantially intact cell structure, the sanitization having been accomplished by methods such as ethylene oxide sanitization and superheated steam sanitization.

Preferred are unmilled psyllium husk particles where the majority of the psyllium husk is retained by an 80 mesh sieve, more preferably where the majority is retained by a 50 mesh sieve, and most preferably where the majority is retained by a 35 mesh sieve.

Compositions of the present invention comprise from 3 w/w % to 15 w/w %, more preferably from 4 w/w % to 10 w/w %, and most preferably from 5% to 8%, such as 6-7%. The oily component is an edible oil, preferably a vegetable oil but also fish oils are preferred. Preferred vegetable oils are coconut oil, corn oil, cottonseed oil, olive oil, palm oil, peanut oil, rapeseed oil, canola oil, linseed oil, safflower oil, sesame oil, soybean oil, and sunflower oil. Nut oils are also applicable to the present invention, including almond oil, cashew oil, hazelnut oil, pecan oil, and walnut oil.

The agglomerating materials useful herein are known in the art. These agglomerating materials are selected from the group consisting of water dispersible hydrolyzed starch oligosaccharide, mono-saccharide, di-saccharide, polyglucose, polymaltose, maltodextrin and mixtures thereof. Compositions of the present invention comprise from about 4% to about 40% of agglomerating material coating on said psyllium husk, preferably from about 10% to about 30%, and more preferably from about 15% to about 25%.

Starches consist of granules separated from edible sources such as potato, arrowroot, oats, wheat, peas, beans, rice, corn, buckwheat, tapioca, rye or barley. A preferred source of starch is corn. The granules exist as a polymeric compound consisting of about 27% linear polymer (amylose) and 73% branched polymer (amylopectin), with these two polymers so associated in the crystal lattice that they are practically insoluble in cold water or alcohol. Starch is soluble in boiling water giving a colloidal solution which may form a jelly on cooling. Hydrolysis of starch may be accomplished by a reaction of either acid, enzymes (e.g., alpha-amylase, beta-amylase or amyloglucosidase), or a combination of the two either together or reacted in series. The hydrolysis will follow different pathway depending on whether acids or enzymes are used. The result is a mixture of oligosaccharides which may be separated for their different properties. The resulting separated water dispersible (preferably soluble) hydrolyzed starch oligosaccharides are classified by their reducing sugar content, i.e., the mono- or di-saccharides such as glucose or fructose. The percent reducing sugar content in the particular hydrolyzed starch oligosaccharide is measured on a weight/weight basis as the Dextrose Equivalent (or "D.E."). Hydrolyzed starch oligosaccharides with a D.E. of from 0 to 20 are called maltodextrins. The solid maltodextrins have low to moderate sweetness, low to moderate hygroscopicity, solubility in water and alcohol, and have reduced browning. Above a D.E. of about 20 the hydrolyzed starch oligosaccharides are called syrup solids. The syrup solids are soluble but have a more noticeable sweetness and are more hydroscopic. Above a D.E. of about 30, the syrup solids become less desirable for use herein. A preferred water dispersible hydrolyzed starch oligosaccharide therefore has a D.E. of from about 0 to about 30. A preferred maltodextrin has a D.E. of from about 5 to about 20, more preferably about 10 (i.e., a reducing sugar content ratio of 10% w/w of the oligosaccharide).

The mono-saccharides are those carbohydrates that in general are aldehyde-alcohols or ketone alcohols that are a hexose or pentose and have a sweet taste. They are readily soluble in water and form crystalline solids. Examples of the mono-saccharides are dextrose, mannose and fructose. The di-saccharides are those carbohydrates which yield two mono-saccharides on hydrolysis. Examples of di-saccharides are lactose, sucrose and maltose.

Polyglucose and polymaltose are those compounds exemplified by U.S. Pat. Nos. 3,766,165 and 3,876,794, incorporated herein by reference in their entirety. A commercially available preparation of a polyglucose is called polydextrose and has a low calorie content (1 Kcal/gram) and little or no sweetness. It is primarily used as a low calorie, bulk replacement for sugar in foodstuffs. Polydextrose is a partially metabolizable, water-soluble polymer prepared by the condensation of a melt which consists of approximately 89% D-glucose, about 10% sorbitol and about 1% citric acid on a weight basis.

Agglomeration techniques are described in the hereinbefore referenced U.S. patents, but preferred is multiple layer coating of the psyllium husk using techniques which result in agglomerating the psyllium husk, e.g., as described in detail in U.S. Pat. Nos. 4,459,280 and 4,548,806, to Colliopoulos et al., incorporated by reference herein; and especially preferred is single layer coating of the psyllium husk in a single pass apparatus whereby an agglomerating material (especially dextrose) is applied as a single coating such that from about 5% to about 20% of water is applied to the psyllium husk during the coating process.

Multiple layer coating of the psyllium husk is accomplished, for example, by using fluid bed agglomerating equipment. An agglomerating material-containing solution is sprayed into this zone to contact the dry oil impregnated psyllium blend. The resulting coated and agglomerated psyllium husk is dropped to a fluid bed dryer where the added solvent is removed. Optional components for the psyllium-containing blend include, but are not limited to, flavoring agents, sweetening agents (preferably low calorie sweetening agents), coloring agents, agglomerating materials (especially maltodextrin) and/or pharmaceutical agents. As noted hereinbefore, it is preferred that the psyllium-containing blend be dry, but it is possible to utilize suitable solvents (e.g., alcohols and/or water) if one is careful, especially if water is utilized, not to cause substantial hydration and swelling of the psyllium, since this is expected to adversely affect the rate at which psyllium husk can interact with water or other fluids.

The compositions of the present invention optionally comprise agents which may be added as a part of the coating and/or as a part of the psyllium-containing blend and/or added to the agglomerated psyllium husk. Preferred is low calorie sweetening agents including, but not limited to, aspartame, saccharine, cyclamate, acesulfame, and mixtures thereof. Another preferred optional component is flavoring agents.

The following example further describes and demonstrates an embodiment within the scope of the present invention. This example is given solely for the purpose of illustration and is not to be construed as limiting the present invention.

EXAMPLE

A quantity of 4.4 kg of canola oil was added to 52.5 kg of whole unmilled psyllium husks. The two components were then mixed mechanically in a rotating blade mixer until the oil was evenly distributed and covered the psyllium seed husks with a fine film.

An aqueous solution of dextrose of 25% was prepared and sprayed onto the oil impregnated psyllium husks when entering an Anhydro type vibrating fluid bed agglomerator. The dextrose solution was pumped at a rate which ensured optimum operating conditions in the fluid bed agglomerator. The dextrose solution was added in an amount which ensured a content of about 18% dextrose in the psyllium-oil-dextrose powder on a weight basis.

The air used to fluidize and dry the particles had an inlet temperature of 116° C. The agglomerated psyllium husks produced had a water content of 4.3% and a density of 310 g/l.

The invention claimed is:

1. An agglomerated oil-impregnated unmilled psyllium husk composition, comprising,
   (a) 50 to 90 w/w % whole unmilled psyllium husk,
   (b) 3 to 15 w/w % of an oil component impregnating the unmilled psyllium husk, wherein the oil component is selected from the group consisting of coconut oil, corn oil, cottonseed oil, olive oil, palm oil, peanut oil, rapeseed oil, canola oil, linseed oil, safflower oil, sesame oil, soybean oil, and sunflower oil, and
   (c) 4 to 40 w/w % of an agglomerating material coating on the oil-impregnated unmilled psyllium husk, wherein the agglomerating material is selected from the group consisting of a water-dispersible hydrolyzed starch oligosaccharide, monosaccharide, disaccharide, polyglucose, polymaltose, maltodextrin and mixtures thereof.

2. Agglomerated psyllium husk according to claim 1, wherein the oil component constitutes from 4 w/w % to 10 w/w % of the agglomerated-oil-impregnated psyllium husk.

3. Agglomerated psyllium husk according to claim 1 comprising from 10 w/w % to 30 w/w % of agglomerating material coating on said psyllium husk.

4. The agglomerated oil-impregnated unmilled psyllium husk composition of claim 1 further comprising 2-10 w/w % maltodextrin.

5. The agglomerated oil-impregnated unmilled psyllium husk composition of claim 1 further comprising 5-10 w/w % molasses.

6. A method for producing the agglomerated oil-impregnated unmilled psyllium husk composition of claim 1, comprising the steps of:
   (a) impregnating unmilled psyllium husk with a thin layer of the oil component,
   (b) coating to agglomerate the oil-impregnated unmilled psyllium with a solution comprising the agglomerating material, and
   (c) drying the agglomerated oil-impregnated unmilled psyllium husk composition.

7. Method according to claim 6, wherein the agglomerated oil impregnated psyllium husk comprise from 4 w/w% to 10 w/w % of the oily component.

8. Method according to claim 6, wherein the husk comprises from about 10 w/w % to about 30 w/w % of agglomerating material coating on said psyllium husk.

* * * * *